(12) United States Patent
Leizerson (10) Patent No.: US 11,435,296 B2
(45) Date of Patent: Sep. 6, 2022

(54) METHOD AND SYSTEM FOR GRADING GEMSTONES

(71) Applicant: DITECH—DIAMOND INSPECTION TECHNOLOGIES LTD., Haifa (IL)

(72) Inventor: Ilya Leizerson, Haifa (IL)

(73) Assignee: DITECH—Diamond Inspection Technologies LTD., Haifa (IL)

( * ) Notice: Subject to any disclaimer, the term of this patent is extended or adjusted under 35 U.S.C. 154(b) by 0 days.

(21) Appl. No.: 17/530,654

(22) Filed: Nov. 19, 2021

(65) Prior Publication Data
US 2022/0155236 A1 May 19, 2022

Related U.S. Application Data

(63) Continuation of application No. PCT/IL2020/050552, filed on May 20, 2020.

(30) Foreign Application Priority Data

May 22, 2019 (IL) .......................................... 266809

(51) Int. Cl.
*G01N 21/87* (2006.01)
*G01N 33/38* (2006.01)
*G01N 21/64* (2006.01)

(52) U.S. Cl.
CPC ............. *G01N 21/87* (2013.01); *G01N 21/64* (2013.01); *G01N 33/381* (2013.01)

(58) Field of Classification Search
CPC ....... G01N 33/381; G01N 21/64; G01N 21/87
See application file for complete search history.

(56) References Cited

U.S. PATENT DOCUMENTS 5,260,772 A * 11/1993 Pollak ................ G01N 21/1717
356/417
2008/0086038 A1* 4/2008 Thornton ................ H01S 3/067
600/310
2017/0241913 A1 8/2017 Gu

FOREIGN PATENT DOCUMENTS

CN 109001205 A * 12/2018
EP 341093 A * 11/1989 ........... B07C 5/3427
(Continued)

OTHER PUBLICATIONS

Written Opinion of the International Searching Authority for PCT/IL2020/050552 dated Aug. 31, 2020.
(Continued)

*Primary Examiner* — Maurice C Smith
(74) *Attorney, Agent, or Firm* — Burns & Levinson, LLP; Joseph M. Maraia (57) ABSTRACT

Gemstone grading method including illuminating the gemstone by light having a plurality of spectral components, each modulated according to a spectrally specific modulation (e.g., of intensity, frequency, phase), collecting the light following interaction with the gemstone, extracting from the collected light a set of intensity values for a respective set of modulation parameter values to provide a transmittance spectrum, and an output indicative of the transmittance spectrum (e.g., color, clarity, fluorescence grade). A complementary system includes a plurality of monochromatic light sources and respective modulators for simultaneously illuminating a gemstone with a modulation spectrally specific for each light source, a detection system for collecting the light following interaction whose signals are fed via a communication system to a data processor configured to extract a set of intensity values for a respective set of modulation parameter values to provide a transmittance spectrum and an output indicative thereof.

20 Claims, 6 Drawing Sheets

(56) References Cited

FOREIGN PATENT DOCUMENTS

| JP | 2004514198 | A | * | 5/2004 | ............... | G07D 7/12 |
| WO | WO-2014055041 | A1 | * | 4/2014 | ............ | G01N 21/87 |
| WO | WO-2018192842 | A1 | * | 10/2018 | ............ | G01N 21/03 |
| WO | 2020/234879 | A1 | | 11/2020 | | |

OTHER PUBLICATIONS

International Search Report for PCT/IL2020/050552 dated Aug. 31, 2020.
International Preliminary Report on Patentability for PCT/IL2020/050552 dated Nov. 16, 2021.

* cited by examiner

| | | | | | | | |
|---|---|---|---|---|---|---|---|
| Cut1 | $T_1(\lambda)$ | D | clarity1 | Cut2 | $T_1(\lambda)$ | D | clarity1 |
| | $T_2(\lambda)$ | E | clarity2 | | $T_2(\lambda)$ | E | clarity2 |
| | ⋮ | ⋮ | ⋮ | | ⋮ | ⋮ | ⋮ |
| | $T_k(\lambda)$ | Z | clarity_k | | $T_k(\lambda)$ | Z | clarity_k |
| Mass1 | $T_1(\lambda)$ | D | clarity1 | Mass2 | $T_1(\lambda)$ | D | clarity1 |
| | $T_2(\lambda)$ | E | clarity2 | | $T_2(\lambda)$ | E | clarity2 |
| | ⋮ | ⋮ | ⋮ | | ⋮ | ⋮ | ⋮ |
| | $T_k(\lambda)$ | Z | clarity_k | | $T_k(\lambda)$ | Z | clarity_k |

METHOD AND SYSTEM FOR GRADING GEMSTONES

CROSS REFERENCE TO RELATED APPLICATIONS

This application is a continuation of International Application No. PCT/IL2020/050552, which designated the United States and was filed May 20, 2020, which claims priority under 35 U.S.C. § 119 or 365 to Israeli Application No. 266809, filed May 22, 2019. The entire teachings of the above applications are incorporated herein by reference.

FIELD AND BACKGROUND OF THE INVENTION

The present invention, in some embodiments thereof, relates to gemology, more particularly, but not exclusively, to a method and system for automatic grading of gemstones.

A major problem facing the gem manufacturer, dealer, grader and jeweler is how to accurately assess and grade the color of a given gemstone. For example, the commercial value of a diamond depends upon the diamond's weight, cut, clarity and color. Highly trained specialists, known as graduate gemologists evaluate these and other stone properties to assess a value or grade for the stone. Small changes in any of these evaluation parameters can translate into a large change in stone price. For example, there has been a large increase in colored diamond traffic in recent years. Color, more than anything else, determines the value of a colored diamond. A small change of hue can mean a price change of thousands of dollars. Because of the sensitivity of gemstone value to grading criteria, in particular color, consistent and reliable grading of gemstones is of particular importance to the industry.

A known color scale for grading white diamonds is the GIA D-to-Z color scale where grades of D through F correspond to colorless diamonds, grades of G through J correspond to diamonds considered as near colorless, grades K through M correspond to diamonds considered faint, grades N through R correspond to diamonds that are very light, and grades S through Z correspond to diamonds that considered light-color. For a white diamond, the lower the grade letter the more valuable the diamond is. Colored diamonds that fall outside the GIA D-to-Z range (namely they are more colored than light-color diamonds) are oftentimes termed "fancy" diamonds, and are more valuable than diamonds graded as D-to-Z diamonds. The color of a fancy diamond is oftentimes graded as one of: fancy-light, fancy, fancy-intense, fancy-dark, fancy-deep, and fancy-vivid.

Several devices have been proposed for measuring colors of gemstones. For example, U.S. Published Application No. 20150233839 discloses a reflectance spectroscopy system including two light sources, a filter, an integrating sphere, and a spectroscopic detection module. Lights from the light sources are filtered by the filter, incident into the interior of the integrating sphere, hit a sample after multiple diffuse reflections in the integrating sphere, and then reflected by the sample to form a reflected light. The reflected light and the diffuse reflections are introduced into the spectroscopic detection module providing photonic information which is then used for generating a spectrogram. Another example is U.S. Pat. No. 7,324,188 which discloses a probe for irradiating a surface of the gemstone with near infrared (NIR) radiation, a radiation transmissive conduit for collecting internally reflected diffuse NIR radiation, and a spectrometer for analyzing the collected radiation.

Other spectroscopy based systems are disclosed in U.S. Published Application No. 20150219567, disclosing determining a parameter based on the detected transmittance of the gemstone, International publication No. WO 2007/069242, disclosing determining a relationship between spectroscopic data and the color quality of a diamond, and International publication No. WO 2016/022153, disclosing analyzing reflected light captured by an imaging device.

Spectroscopy based commercial systems for grading gemstone colors are marketed by Zvi Yehuda Ltd., Israel, and by OGI Systems Ltd., Israel. Additional background art includes U.S. Pat. No. 7,580,118, Hardie et al., 2016, arXiv: 1606.02774, and O'Toole et al., Sensors 2008, 8, 2453-2479, and

SUMMARY OF THE INVENTION

According to an aspect of some embodiments of the present invention there is provided a system for grading gemstones. The system comprises: a plurality of monochromatic light sources arranged to illuminate a gemstone; a light modulator for modulating light emitted by each light source to provide illumination that is modulated according to a spectral-specific modulation; a light detection system for collecting light following interaction of the illumination with the gemstone; and a communication system configured to communicate signals from the light detection system to a data processor for extracting from the signals a set of intensity values for a respective set of modulation parameter values to provide a transmittance spectrum, and for generating an output indicative of the transmittance spectrum.

According to some embodiments of the invention the light modulator is configured to provide modulation according to the same modulation scheme, but using different values of the modulation parameter for different spectral components of the light.

According to some embodiments of the invention the modulator is configured to modulate the light such that modulations of different spectral components are characterized by a different modulation frequency.

According to some embodiments of the invention a modulation frequency of each modulation is other than a frequency of an electric power grid operating in a vicinity of the system, and other than each harmonic of the electric power grid.

According to some embodiments of the invention the light detection system comprises a pixilated light sensor configured to sense different spectral components by different pixels of the sensor.

According to an aspect of some embodiments of the present invention there is provided a system for grading gemstones. The system comprises: a plurality of monochromatic light sources arranged to simultaneously illuminate a gemstone by light; a light detection system for collecting light following interaction of the light with the gemstone, the light detection system having a pixilated light sensor configured to sense different spectral components by different pixels of the sensor; and a communication system configured to communicate signals from the light detection system to a data processor for extracting from the signals a transmittance spectrum, and for generating an output indicative of the transmittance spectrum.

According to some embodiments of the invention the system comprises the data processor.

According to some embodiments of the invention the system comprises a light modulator for modulating light emitted by each light source to provide modulated illumination according to the same modulation scheme, and using the same modulation parameter for all light sources.

According to some embodiments of the invention the light sources comprise at least one ultraviolet light source, and wherein the output comprises a fluorescence strength of the gemstone.

According to some embodiments of the invention the system comprises a reference light detection system for collecting light that does not interact with the gemstone, wherein the data processor is configured for receiving reference signals from the reference light detection system and calibrating the transmittance spectrum or the output based on the reference signals.

According to some embodiments of the invention the data processor is configured to calculate a clarity grade of the gemstone based on the reference signals, and wherein the output is also indicative of the clarity According to some embodiments of the invention the data processor is configured for calibrating the transmittance spectrum or the output based on pre-recorded calibration data.

According to some embodiments of the invention the data processor is configured to calculate a clarity grade of the gemstone based on the pre-recorded calibration data, and wherein the output is also indicative of the clarity.

According to some embodiments of the invention the system comprises a cavity for holding the gemstone.

According to some embodiments of the invention the cavity is open.

According to some embodiments of the invention the light sources are arranged peripherally with respect to the gemstone.

According to some embodiments of the invention the light sources are arranged in an interlaced manner to define a plurality of light source groups, wherein for each group there are at least two light sources that provide different spectral components.

According to some embodiments of the invention the system comprises a light manipulating element positioned at a light path of light to be detected by the detection system.

According to some embodiments of the invention the light manipulating element comprises at least one optical element selected from the group consisting of a polarizer, a diffuser, a lens, a filter, and a refractor.

According to some embodiments of the invention the data processor is a central processing unit of a mobile device.

According to some embodiments of the invention the system comprises at least one of a tweezers, and a cleaning device.

According to some embodiments of the invention the system comprises at least one testing sample or gemstones.

According to an aspect of some embodiments of the present invention there is provided a method of grading a gemstone. The method comprises: illuminating the gemstone by light having a plurality of spectral components, each modulated according to a spectral-specific modulation; collecting light following interaction of the light with the gemstone; extracting from the collected light a set of intensity values for a respective set of modulation parameter values to provide a transmittance spectrum; and generating an output indicative of the transmittance spectrum.

According to some embodiments of the invention the spectral-specific modulation is selected from the group consisting of frequency modulation and phase modulation.

According to some embodiments of the invention each spectral component is modulated according to the same modulation scheme, but using different values of the modulation parameter for different spectral components.

According to some embodiments of the invention the spectral-specific modulation comprises intensity modulation.

According to some embodiments of the invention different spectral components are modulated using different modulation frequencies.

According to some embodiments of the invention each modulation frequency is other than a frequency of an electric power grid operating in a vicinity of the system, and other than each harmonic of the electric power grid.

According to some embodiments of the invention the light is collected by a pixilated light sensor configured to sense different spectral components by different pixels of the sensor.

According to an aspect of some embodiments of the present invention there is provided a method of grading a gemstone. The method comprises: simultaneously illuminating a gemstone by light having a plurality of spectral components; collecting light following interaction of the light with the gemstone by a pixilated light sensor configured to sense different spectral components by different pixels of the sensor and to responsively provide separate signals; extracting from the signals a transmittance spectrum; and generating an output indicative of the transmittance spectrum.

According to some embodiments of the invention the method comprises modulating the light according to the same modulation scheme, and using the same modulation parameter for all spectral components.

According to some embodiments of the invention the output comprises a color grade of the gemstone.

According to some embodiments of the invention the output comprises a graphical representation of the transmittance spectrum.

According to some embodiments of the invention the method comprises collecting reference light that does not interact with the gemstone, and calibrating the transmittance spectrum or the output based on the reference light.

According to some embodiments of the invention the method comprises calculating a clarity grade of the gemstone based on the reference signals, wherein the output is also indicative of the clarity.

According to some embodiments of the invention the method comprises calibrating the transmittance spectrum or the output based on pre-recorded calibration data.

According to some embodiments of the invention the method comprises calculating a clarity grade of the gemstone based on the pre-recorded calibration data, wherein the output is also indicative of the clarity.

According to some embodiments of the invention the method comprises placing the gemstone in an open cavity prior to the interaction with the light, wherein the illumination is executed while the cavity is open.

According to some embodiments of the invention the illumination is by a plurality of arranged peripherally with respect to the gemstone.

According to some embodiments of the invention the illumination is by a plurality of arranged in an interlaced manner to define a plurality of light source groups, wherein for group there are at least two light sources that provide different spectral components.

According to some embodiments of the invention the method comprises a manipulating the light following the interaction and prior to the collecting.

According to some embodiments of the invention the manipulating comprises at least one of: polarizing, diffusing, focusing, collimating, filtering, and refracting.

According to some embodiments of the invention the extracting and the generating the output is by a central processing unit of a mobile device.

According to some embodiments of the invention the gemstone is a cut diamond.

According to some embodiments of the invention the gemstone is a rough diamond.

According to some embodiments of the invention the method comprises transmitting the output to a remote location.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to gemology, more particularly, but not exclusively, to a method and system for automatic grading of gemstones.

The inventor of the present invention found that while several systems successfully grade the color of gemstones these systems are costly. For example, due to the high cost of spectroscopic equipment, the spectroscopy based commercial systems are expensive reaching several tens of thousands of U.S. dollars.

The inventor of the present invention also found that while conventional systems can grade the color of rough gemstones, they fail to provide an accurate grade value when confronted with cut polished gemstones. The inventor realized that such a drawback forces the end users (e.g., gem dealers, jewelers, insurance agents) to employ manual techniques to estimate the value of a cut polished gemstone.

The inventor has therefore devised a grading technique that is simpler, less expensive, and at least as accurate as the systems described in the aforementioned references.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

At least part of the processing operations described herein can be implemented by a data processor, e.g., a dedicated circuitry or a general purpose computer, configured for receiving data and executing the operations described below. At least part of the processing operations described herein can be implemented by a data processor of a mobile device, such as, but not limited to, a smartphone, a tablet, a smartwatch and the like, supplemented by software app programed to receive data and execute processing operations. At least part of the processing operations can be implemented by a cloud-computing facility at a remote location.

Computer programs implementing the processing operations of the present embodiments can commonly be distributed to users by a communication network communicating with a dedicated storage facility or a cloud storage facility storing the programs, or on a distribution medium such as, but not limited to, a flash memory device and a portable hard drive. From the communication network or distribution medium, the computer programs can be copied to a hard disk or a similar intermediate storage medium. The computer programs can be run by loading the code instructions either from their distribution medium or their intermediate storage medium into the execution memory of the computer, configuring the computer to act in accordance with the method of this invention. All these operations are well-known to those skilled in the art of computer systems.

Processing operations described herein may be performed by means of processer circuit, such as a DSP, microcontroller, FPGA, ASIC, etc., or any other conventional and/or dedicated computing system.

The processing operations of the present embodiments can be embodied in many forms. For example, they can be embodied in on a tangible medium such as a computer for performing the operations. They can be embodied on a computer readable medium, comprising computer readable instructions for carrying out the method operations. They can also be embodied in electronic device having digital computer capabilities arranged to run the computer program on the tangible medium or execute the instruction on a computer readable medium.

Figure 1A:
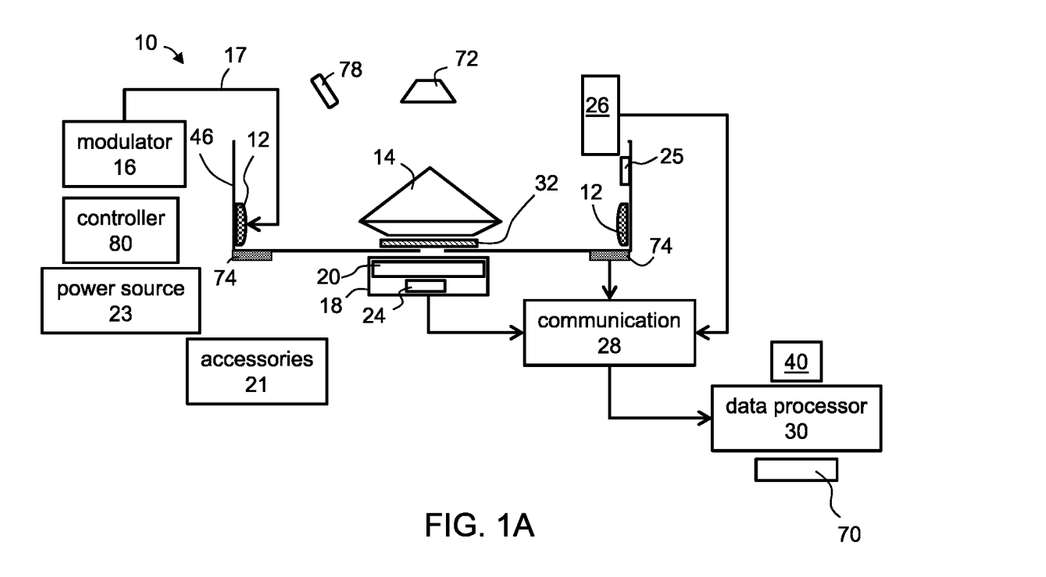
FIGS. 1A-C are schematic illustrations of a system for grading gemstones, according to some embodiments of the present invention.
Figure 1B:
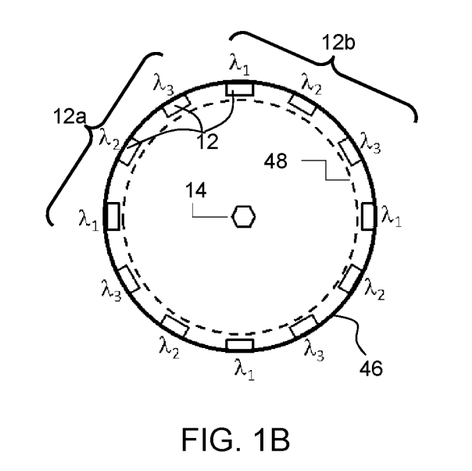
Figure 1C:
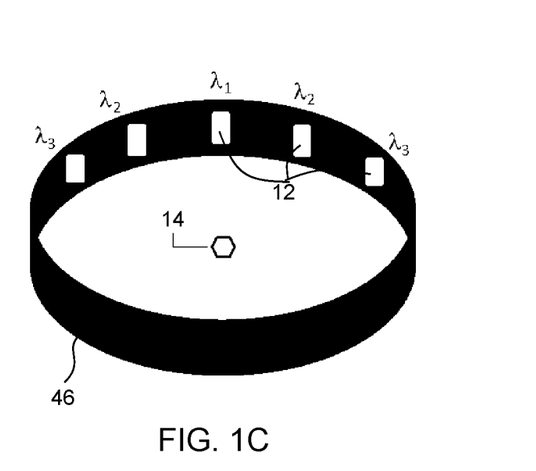

Referring now to the drawings, FIGS. 1A-C are schematic illustrations of a system 10 for grading gemstones, according to some embodiments of the present invention. System 10 comprises a plurality of monochromatic light sources 12 arranged to illuminate a gemstone 14 by light. The light sources and other active elements of system 10 as detailed herein can be powered by a power source 23, which can be a battery or a power outlet of electric power grid.

Gemstone 14 is preferably a diamond, more preferably a cut polished diamond, but may in some embodiments of the present invention be another type of gemstone, including, without limitation, a rough diamond, a ruby, am emerald, a sapphire and the like. Optionally, system 10 is provided with one or more accessories 21, such as, but not limited to, a tweezers, a cleaning device, one or more testing samples or gemstones, and the like. System 10 can comprise a cavity 46 in which gemstone is placed for its analysis. Preferably, cavity 46 is open. The advantage of this embodiment is that it allows fast replacement of gemstones with the cavity allowing fast serial analysis of multiple gemstones. Alternatively cavity 46 can include a lid or a cover (not shown) for blocking ambient light from entering the cavity.

Each light source 12 optionally and preferably emits a monochromatic light, preferably, but not necessarily, within a bandwidth of less than 50 nm or less than 40 nm e.g., about 25 nm. It was found by the inventor of the present invention that such a bandwidth is advantageous for grading gemstones both from the standpoint of sensitivity and from the standpoint of simplicity.

Each of light sources 12 may independently include any type of light emitting element, possibly based on a semiconductor, such as, but not limited to, a light emitting diode (LED) packaged or un-packaged die, or a laser diode (LD), or a vertical-cavity surface-emitting laser (VCSEL) packaged or un-packaged die, or an organic LED (OLED) packaged or un-packaged die, or a quantum dot (QD) lamp, or the like.

Typically, light sources 12 emit light in the visible range (e.g., from about 400 nm to about 700 nm), but other optical ranges, such as, but not limited to, the near-infrared range (e.g., from about 700 nm to about 1.4 μm) or the infrared range (e.g., from about 700 nm to about 100 μm) or in the UV range (e.g., from about 200 nm to about 400 nm), are also contemplated in some embodiments of the present invention.

Preferably, the light sources are selected to be eye-safe.

In preferred embodiments of the present invention, all light sources 12 emit light simultaneously.

The inventor also contemplate light sources that emit light in the ultraviolet range (e.g., from about 200 nm to about 400 nm). The advantage of these embodiments is that ultraviolet light can induce fluorescence in gemstone 14, thereby providing more information regarding its characteristics and color. In embodiments in which ultraviolet light is emitted, the ultraviolet light is optionally and preferably used in conjugation with visible and/or infrared light. This can be done either sequentially wherein the ultraviolet light sources are activated before or after the activation of the visible and/or infrared light sources, or simultaneously wherein ultraviolet light sources as well as the visible and/or infrared light sources are all activated together. The grades of fluorescence strength may be in accordance to a standard grade (none, faint, medium, strong, very strong in GIA) or other.

The activation and deactivation of the light sources, as well as the operation of other components of system 10 described below are preferably controlled by a controller 80, having an electronic circuit configured for performing the operations described herein.

Light sources 12 are preferably arranged peripherally with respect to gemstone 14, for example, generally circularly with similar distances (e.g., with tolerance of less than 20%) from the center of cavity 46. A representative example of a peripheral distribution of light sources 12, according to some embodiments of the present invention, is illustrated in FIGS. 1B and 1C. In the illustrated embodiment, several sets of light sources are arranged in an interlaced manner to define a plurality of light source groups 12a, 12b, etc. Each set of light sources provide illumination characterized by the same or similar central wavelength, and light sources of different sets provide illumination characterized by different central wavelength. For example, a first set of light sources provides illumination characterized by a central wavelength $\lambda_1$, a second set of light sources provides illumination characterized by a central wavelength $\lambda_2$, etc., where $\lambda_1$, $\lambda_2$, etc. have different values.

The sets of light sources are arranged in groups 12a, 12b, etc., in an interlaced manner in the sense that for each group there are at least two light sources of different sets (hence provide illumination at different wavelengths). Preferably, the groups are constructed to provide homogeneous illumination of gemstone 14. In the embodiment illustrated in FIG. 1B, for each of the wavelengths $\lambda_1$, $\lambda_2$, etc. provided by sources 12, a source illuminating in the respective wavelength is included in each of the light source groups 12a, 12b, etc.

The density of light sources along the periphery can be selected based on a desired homogeneity of the light and/or desired illumination light power. In some embodiments of the present invention system 10 can comprise a peripheral (e.g., cylindrical) optical element 48 along the periphery of cavity 46. Peripheral optical element 48 can include at least one of a diffuser, an optical filter to pass specific wavelengths, a lens, a spatial filter, a non-homogeneous diffuser, a cylindrical lens surrounding all light sources, and multiple cylindrical lenses mounted on each light source. More than one type of optical elements 48 may be mounted in the cavity.

System 10 optionally and preferably comprises a light modulator 16 configured to control light sources 12, so as to modulate the light emitted by each one of light sources 12. The operation of light modulator 16 is optionally and preferably controlled by controller 80. The modulation employed by modulator 16 can be direct modulation or indirect modulation. When direct modulation is employed, the respective light source receives a modulation signal from modulator 16 and generates a modulated light beam. When indirect modulation is employed, an unmodulated light beam is generated by the respective light source and modulator 16 receives the unmodulated light beam and provides a modulated light beam according to a modulation scheme.

In the schematic illustration of FIG. 1A, which is not to be considered as limiting, modulator 16 provides direct modulation by means of modulation signals transmitted to light sources 12. In the shown configuration, modulator 16 is external to light sources 12 and is in communication, preferably electrical communication, with light sources 12 (representative communication shown at 17). However, this need not necessarily be the case, since, for some applications, each light source 12 is provided as an integrated (e.g., monolithic) unit which comprises both the light emitting element and the light modulator (which can provide direct or indirect modulation). In these applications, light modulator 16 is embodied as a plurality of sub-units, each being integrated in a respective light source 12. Also contemplated are embodiments in which modulator 16 is external to light sources 12 and provides indirect modulation. In these embodiments, modulator 16 is preferably positioned at the optical paths between sources 12 and gemstone 14.

In preferred embodiments of the present invention, the modulations of light sources 12 are not synchronized thereamongst.

In various exemplary embodiments of the invention the modulator 16 ensures that each of light sources 12 provides illumination that is modulated according to a spectral-specific modulation.

The modulation is referred to as "spectral-specific" in the sense that each spectral component of the light (within a wavelength-band characteristic to the respective light source) is modulated differently. Typically, the modulations provided by modulator 16 are represented by set of independent functions that can be separated and distinguished by signal processing as further detailed hereinbelow.

Different modulations can be realized as different modulation schemes (e.g., different property of the optical field being modulated, and/or a different modulation function is employed for the modulation), or as the same modulation scheme but using different values for the parameter that characterizes the same modulation (e.g., different modulation frequency, or different modulation phase, or different modulation duty cycle, or the like).

Preferably, the spectral-specific modulation comprises intensity modulation. Alternatively, or additionally the spectral-specific modulation can include one or both of a frequency modulation and a phase modulation.

In some embodiments of the present invention the spectral-specific modulation is sinusoidal modulation. In some embodiments of the present invention modulator 16 modulates the light such that modulations of different spectral components (light portions within different wavelength bands, e.g., emitted by light sources belonging to different sets, see FIG. 1B) are characterized by a different modulation frequency. These modulation frequencies are denoted herein by $f_1, \ldots, f_N$. A representative example of a frequency range from within each of the modulation frequencies $f_1, \ldots, f_N$ can be selected, includes, without limitation, the frequency range of from about 100 Hz to about 1 kHz. Typically, but not necessarily, none of the modulation frequencies is a harmonic of any other modulation frequency. In other words the modulation frequencies are selected such that the ratio between any pair of modulation frequencies is non-integer.

Preferably, each of the modulation frequencies is other than a frequency of an electric power grid operating in a vicinity of system 10, and other than each harmonic of the electric power grid. Thus, for example, when system 10 operates in Europe or the Middle East the modulation frequency is other than 50 Hz and also other than integer multiplication of 50 Hz, and when system 10 operates in the USA the modulation frequency is other than 60 Hz and also other than integer multiplication of 60 Hz. The advantage of these embodiments is that they reduce the likelihood of errors due to interferences by the electric power grid.

The light from sources 12 interacts with gemstone 14. Typically, the light experiences absorption and one or more refractions and reflections within gemstone 14, before exiting gemstone 14. In some cases, the light also experiences diffraction within gemstone 14 or near its sharp edges. The spectral contents of the light following the interaction with gemstone 14 depend on the optical properties of gemstone 14, particularly its color and transparency.

Optionally and preferably, system 10 also comprises a light detection system 18 for collecting the light following the interaction of the light from sources 12 with gemstone 14.

The operation of light detection system 18 is optionally and preferably controlled by controller 80. Preferably, gemstone 14 is positioned in cavity 46 in a manner that blocks stray light (e.g., light that does not pass through gemstone 14) from entering system 20. Light detection system 18 comprises an active optical element 20 that produces a signal (typically, an electrical signal) in response to light incident thereon. Active optical element 20 can be of any type that is responsive to the range of wavelengths of the light emitted by sources 12. Representative examples of active optical elements that can be employed by light detection system 18 include, without limitation, a photodiode, an avalanche photodiode, a photovoltaic cell, a light dependent resistor (LDR), a photomultiplier, and the like. In some embodiment, detecting system 18 comprises an optical fiber or other optical waveguide (not shown) for guiding the gathered light from cavity 46 to Active optical element 20.

In some embodiments of the present invention, system 18 detects all spectral components of the light without providing information regarding the identity (e.g., wavelength) of the respective component.

Figure 2A:
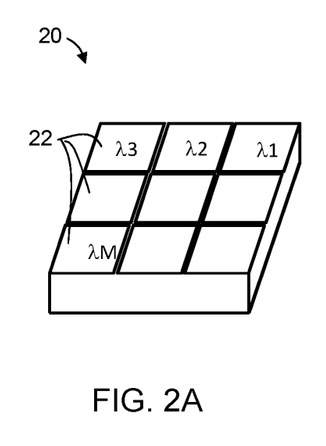
FIG. 2A is a schematic illustration of a pixilated light sensor having a plurality of wavelength-selective pixels, according to some embodiments of the present invention.
Figure 2B:
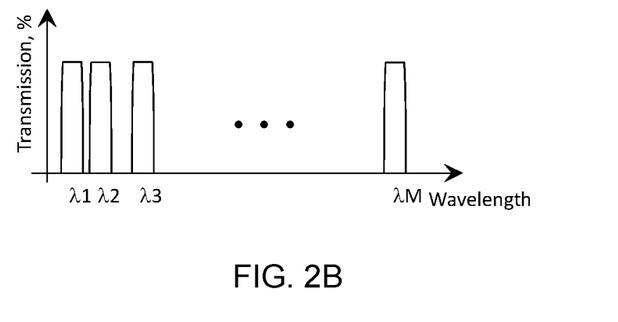
FIG. 2B is a schematic illustration of a selectivity of each pixel of the pixilated light sensor shown in FIG. 2A, according to some embodiments of the present invention.

Alternatively, optical element 20 of system 18 can be a pixilated light sensor configured to sense different wavelengths by different pixels of the sensor. These embodiments are illustrated in FIGS. 2A and 2B. Shown in FIG. 2A is a pixilated light sensor 20 having a plurality of wavelength-selective pixels 22. Each wavelength-selective pixel is covered with a wavelength-selective optical filter that transmits a specific predefined wavelength range, or includes a wavelength-selective active element that is sensitive to a specific predefined wavelength band. The centerline of specific predefined wavelength band is denoted $\lambda_1, \lambda_2, \ldots, \lambda_M$.

The selectivity of each pixel is schematically illustrated in FIG. 2B, for the case in which wavelength-selective optical filter is used. Shown is the transmission coefficient for each wavelength band. The ordinarily skilled person would know how to express the selectivity for the case of a wavelength-selective active element, e.g., using the sensitivity of the respective active element instead of the transmission coefficient. It is appreciated that FIG. 2B is a synthetic illustration and that some spectral overlap and/or deviation in the transmission coefficient may exist among different filters, but this has little effect on the ability of system to grade gemstone 14, as will be explained below.

Thus, when the light incidents on optical element 20, a wavelength-selective pixel covered by a filter whose centerline is $\lambda_1$, or having an active element whose centerline is $\lambda_1$, generates a signal only in response to those spectral components of the light that fall within the wavelength range centered at $\lambda_1$, a wavelength-selective pixel covered by a filter whose centerline is $\lambda_2$, or having an active element whose centerline is $\lambda_2$, generates a signal only in response to those spectral components of the light that fall within the wavelength range centered at $\lambda_2$, and so on. This allows light detection system 18 to spectrally decompose the light into a plurality of channels, hence provide information regarding the spectral contents of the light. Pixilated light sensors such as the sensor illustrated in FIGS. 2A and 2B are commercially available, for example, from PIXELTEQ, USA.

Use of pixilated light sensor with wavelength-selective pixels allows simultaneous detection of the contributions to multiple wavelength bands operated by the same modulation frequency or by other parameter.

Optionally, system 18 also comprises an Analog to Digital (A2D) circuit 24 converting the analog signals provided by active element 18 into digital signals. In some optional embodiments, system 10 also comprises a reference light detection system 26 for collecting light from light sources 12 that does not interact with gemstone 14. The operation of reference light detection system 26 is optionally and preferably controlled by controller 80. Reference light detection system 26 can be of any type described above with respect to light detection system 18. Preferably, systems 18 and 26 are of the same type. The signals provided by light detection system 26 (in embodiments in which system 26 is employed) are optionally and preferably used for calibration, as further detailed hereinbelow.

Optionally, system 10 comprises a light manipulating element 32 positioned at a light path of the light to be detected by detection system 18 and/or detection system 26. Light manipulating element 32 can be of any type, such as, but not limited to, a polarizer configured for polarizing the light, a diffuser configured for diffusing the light, a lens configured for focusing or collimating the light, a filter configured for filtering out selected spectral components, a refractor (e.g., a transparent window) configured for refracting the light, and any combination thereof. In embodiments in which the light sources comprise one or more ultraviolet light source for inducing fluorescence, light manipulating element 32 is preferably selected to block ultraviolet light from arriving at detection system 18.

System 10 can additionally comprise a communication system 28 that communicates signals from detection system 18 and detection system 26 (in embodiments in which system 26 is employed) to a data processor 30. The operation of communication system 28 and optionally also of data processor 30 is optionally and preferably controlled by controller 80. Preferably, data processor 30 is also part of system 10.

In some embodiments of the present invention system 10 comprises a thermometer 25 constituted for measuring the temperature of cavity 46, Preferably, thermometer 25 transmits to data processor 30 over communication system 28 signals pertaining to the temperature of cavity 46. As further described below, data processor 30 optionally and preferably generates an output indicative of a calculated transmittance spectrum. When data processor 30 receives signals pertaining to the temperature of cavity 46, data processor 30 optionally and preferably uses the temperature for correcting the calculated transmittance spectrum.

Thermometer 25 is illustrated in FIG. 1 as a separate device mounted on the wall of cavity 46. However, this need not necessarily be the case, since, for some applications, it may not be necessary for the thermometer to be a separate device or to be mounted directly on the wall of the cavity. For example, thermometer can be mounted on a base of cavity 46, or alternatively or additionally be integrated within another component of system 10, such as, but not limited to, power source 23, light sources 12, detection system 18 and/or detection system 26. Further contemplated are embodiments in which more than one thermometer is employed, each mounted at a different part of cavity 46 or integrated within a different component of system 10.

Communication system 28 can employ wireless communication, such as, but not limited to, WiFi, Bluetooth®, and wireless telephony protocols such as GSM. Alternatively or additionally, communication system 28 can employ wired communication, e.g., via USB ports or the like.

In some embodiments of the present invention data processor 30 is, or comprises, a data processor of a mobile device, such as, but not limited to, a smartphone, a tablet, a smart watch and the like.

When detection system 18 and detection system 26 (if employed) provide digital signals, communication system 28 communicates the digital signals to processor 30.

When detection system 18 and detection system 26 (if employed) provide analog signals, processor 30 preferably comprises an A2D circuit for receiving the analog signals from communication system 28 and converting them to digital signals.

Data processor 30 optionally and preferably extracts from the signals a set of intensity values for a respective set of modulation parameter values. For example, when the modulation parameter is a modulation frequency, data processor 30 extracts from the signals an intensity value for each value of the modulation frequency. The extraction of the set of intensity values can be done by an appropriate computerized procedure that receives a signal and decomposes it according to the respective parameter. In embodiments in which the modulation parameter is a modulation frequency, data processor 30 can employ, for example, a Fourier analysis, to extract the frequency content of the modulation.

When data processor 30 receives signals also from reference light detection system 26, the signals from system 26 can be used for calibrating the set of values, based on the relation between the signals from system 18 and the signals from system 26. The calibration is typically executed to provide a transmittance value for each intensity value of each particular wavelength band. Generally, the signals from system 26 provide processor 30 with information regarding the light intensities provided by the light sources 12. Therefore, by comparing the set of intensity values extracted from the signals received from system 26 with the set of intensity values extracted from the signals received from system 18 for each particular wavelength band, a calibrated transmittance spectrum 36, comprising the transmittance of the gemstone for each wavelength, can be generated.

When system 26 is not employed, system 10 is optionally and preferably operated firstly without gemstone 14, to allow data processor 30 to receive signals that describe the light intensities provided by the light sources 12. Data processor 30 can store these signals in a computer-readable medium as pre-recorded calibration data. In other embodiments the calibration is evaluated with a reference sample for which the transmittance as a function of the wavelength is known. Thereafter, system 10 can be operated with gemstone 14, and data processor 30 can calibrate the transmittance spectrum of gemstone 14 using the pre-recorded calibration data, as described above with respect to the signals from system 26.

Figure 3:
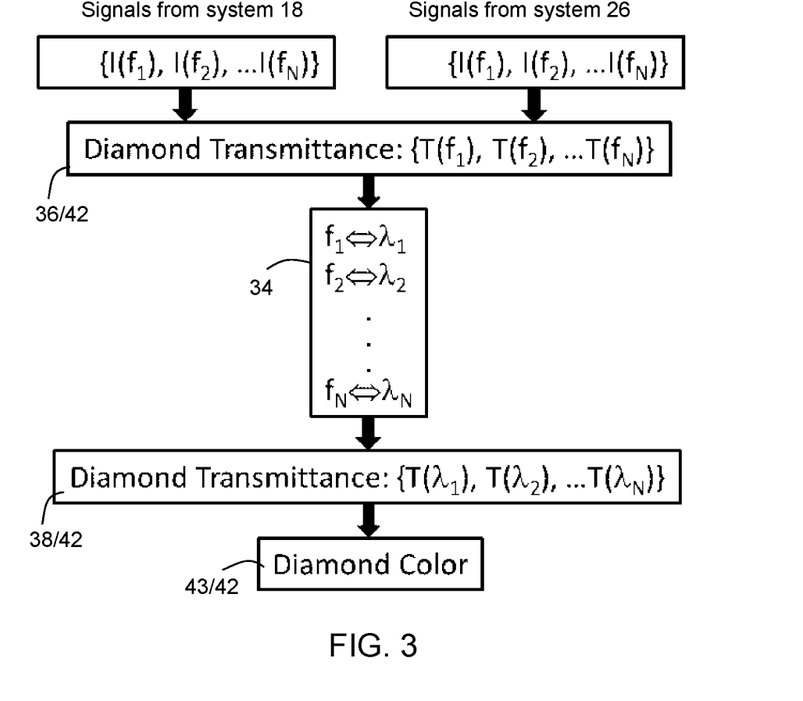
FIG. 3 is a schematic diagram illustrating a process for determining a color of a gemstone (e.g., a diamond), for a non-limiting case in which a modulation parameter is a modulation frequency, according to some embodiments of the present invention.

Once the transmittance spectrum as a function of the modulation parameter is extracted, data processor 30 optionally and preferably associates each value of the parameter to a spectral component of the light. Due to the spectral specificity of the modulation, such an association is readily obtainable. Each spectral band is attributed to a specific modulation. The parameters describing the intensity at the specific modulation among the variety of the modulations can thus be associated with the light intensity of the specific wavelength band. Alternatively, the association can be done using a lookup table mapping the spectral-specific modulations to the spectral components of the light. The process is illustrated in FIG. 3, for the non-limiting case in which the modulation parameter is the modulation frequency. As illustrated, the transmittance spectrum T(f) 36 of the gemstone (diamond, in the present example) is extracted based on the intensity values I for each individual frequency f, as received from systems 18 and 26 (or, when system 26 is not employed, based on the pre-recorded calibration data and the intensity values as received from system 18). A computer readable medium storing a lookup table 34 is then accessed to associate each modulation frequency with a wavelength (or, equivalently, an optical frequency). Based on the association, the transmittance spectrum T(λ) 38 as a function of the wavelength λ is obtained.

In some embodiments of the present invention data processor 30 generates an output 42 indicative of the transmittance spectrum. The output can be displayed on a display device 40. When data processor 30 is associated with a mobile device, display 40 can be the display of the mobile device. The display can also be at a remote location in which case data processor 30 transmits the output 42 to the remote display over a wired or wireless communication network.

In some embodiments of the present invention output of system 10 is evaluated at a remote location. In some embodiments of the present invention a gemstone is examined by a remote user while the gemstone is introduced to the system by a local user such as assistant. The measurement information can then be shared with the remote user.

Figure 4:
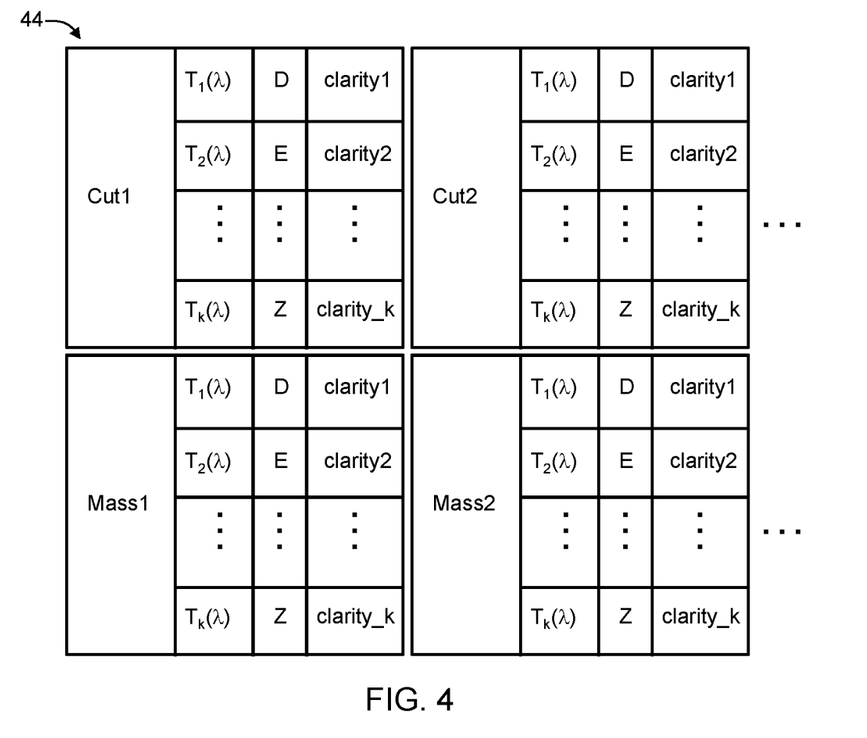
FIG. 4 is a schematic illustration of a library suitable for some embodiments of the present invention.

The output generated by data processor 30 can be, for example, a graphical representation of the transmittance spectrum 36 (as a function of the modulation frequency) and/or 38 (as a function of the wavelength or optical frequency). The output can also be a color grade 43 of gemstone 14. In these embodiments, the data processor determines the color grade based on the obtained transmittance spectrum 36 or 38. This can be done, for example, by accessing a computer readable medium storing a library of transmittance spectra and associated color grades. A representative illustration of a library 44 suitable for the present embodiments is shown in FIG. 4. In this representative illustration, the library associates a transmittance spectrum as a function of the wavelength to a color grade according to the GIA D-to-Z color scale. However, this need not necessarily be the case, since, for some applications, it may not be necessary for the transmittance spectrum to be as a function of the wavelength (e.g., it can be as a function of the modulation parameter, e.g., modulation frequency), and since for some applications, it may not be necessary for the color grade to be according to the GIA D-to-Z color scale (e.g., it can include less grades, for example, D-to-M, corresponding to colorless to faint diamonds, or some other color scale, such as, but not limited to, a color scale for colored diamonds).

It is expected that during the life of a patent maturing from this application many relevant color grading scales will be developed and the scope of the term color grade is intended to include all such new technologies a priori.

The library can be stored in a computer readable medium connected to data processor 30, or at a remote location, such as, but not limited to, a cloud storage facility or the like. The library can be an updatable library that is routinely updated by receiving information from system 10 or a user input.

In use, data processor searches library 44 for a library-stored transmittance spectrum that best matches the obtained transmittance spectrum, and pulls from library 44 the color grade associated with the library-stored transmittance spectrum. Also contemplated, are embodiments in which library 44 associates between transmittance spectra and gemstone clarity grades (shown in FIG. 4 as grades clear1, clear2, etc.). This allows system 10 also to determine the clarity grade of the gemstone. Thus, data processor can search library 44 for a library-stored transmittance spectrum that best matches the obtained transmittance spectrum, and pull from library 44 the gemstone clarity grade associated with the library-stored transmittance spectrum. The library can associate a transmittance spectrum to a clear grade according to any known scale, e.g., the numerical American Gem Society clarity scale (1 to 10), the GIA clarity scale (Flawless/IF, VVS1, VVS2, VS1, VS2, SI1, SI2, I1, I2, I3), or the like.

In some embodiments of the present invention library 44 also include entries pertaining to other properties of the gemstone 14, including, without limitation, at least one of: a gemstone cut, and/or a gemstone mass, wherein for each of a plurality of such properties, library 44 associates between transmittance spectra and color and/or clarity grades. In the schematic illustration of FIG. 4, which is not to be construed as limiting, library 44 include entries pertaining to gemstone cuts, and entries pertaining to gemstone masses wherein for each of a plurality of gemstone cuts Cut1, Cut2, etc., and each of a plurality of gemstone masses Mass1, Mass2, etc., and library 44 associates between transmittance spectra and color and/or clarity grades. Other parameters that can be included in the library include, without limitation, one or more of: fluorescence strength, mining origin and proportion quality.

The inventor contemplates many cuts to be included in library 44. Representative example include, without limitation, a Heart cut, an Emerald cut, a Radiant cut, a Rectangle cut, a Princess cut, a Marquise cut, a S. French Marquise cut, an Oval cut, a Cushion cut, a Pear cut, a Pearmirage cut, a French Pearmirage cut, a French Pear cut, a French Marquiz cut, a Round Asscher cut, a Trilliant cut, a Octahedron cut, a Sawable cut, a Cleavage cut, a Makable cut, a Flat cut, a Crystal cut, Maacle cut, a Round Brilliant cut, an Oval Brilliant cut, a Rose Cut, rough diamond, and any variant thereof. Thus, for example, library 44 can include a plurality of spectra and associated gemstone characteristics (color grades and/or clarity grades) for a Heart cut, another plurality of spectra and associated gemstone characteristics for an Emerald cut, an additional plurality of spectra and associated gemstone characteristics for a Radiant cut, an additional plurality of spectra and associated gemstone characteristics for a rough diamond etc.

Inclusions of the additional gemstone properties in library 44 allows system 10 also to determine the gemstone characteristics (color grade or clarity grade) of the gemstone for a given gemstone property of the gemstone 14. Data processor 30 can receive a gemstone property (e.g., a cut and/or a mass), and access those parts of the library that correspond to the input property for determining the gemstone characteristics.

The input pertaining to the gemstone property can in some embodiments of the present invention be provided to data processor 30 as a user input. Specifically, the user can be presented, e.g., on a user interface device 70 of data processor 30, with a list of gemstone properties (e.g., a list of cuts and/or a list of masses), and select using user interface device 70 one or more of the gemstone properties. Data processor 30 can then receive the selected property from user interface device 70. When processor 30 is a data processor of a mobile device, display 40 can be a touchscreen and serve as user interface device 70.

The input pertaining to the gemstone property can be obtained automatically by system 10. For example, in some embodiments of the present invention system 10 comprises an imaging system 72 positioned to allow imaging system 72 to capture an image of gemstone 14. The operation of imaging system 72 is optionally and preferably controlled by controller 80.

The image provided by system 72 can be a video image or a stills image, and can be a two-dimensional or three-dimensional image. Image data generated by imaging system 72 can be transmitted to data processor 30 by system 28 (communication path not shown). In other embodiments, data processor 30 can access a computer readable medium storing an image of gemstone 14, in which case it is not necessary for the system to include a dedicated imaging system. For example, the user can capture an image of the gemstone 14 using a separate camera (e.g., a camera of a smartphone). This image can be stored in a computer readable medium accessible to processor 30.

Data processor 30 is preferably provided with image processing capabilities and is configured to process the image data so as to determine the cut type and its proportions of gemstone 14. Such determination can be done, for example, by comparing the image data with at least one reference image data, and determining the cut based on the comparison. Optionally, processor 30 can assign a cut grade to gemstone 14 based on differences between the image data and the reference image data, and generate output pertaining to the shape grade on display 40. The captured image may optionally and preferably also be used for assessing the mass of gemstone 14 based on the evaluated cut. Suitable techniques for determining a gemstone's cut and cut grade are described in international patent publication No. 2014141282 and in U.S. Pat. No. 9,151,717, the contents of which are hereby incorporated by reference.

In some embodiments of the present invention system 10 comprises a gemstone scale 74 arranged to weigh gemstone 14, and provide signals pertaining to its mass (e.g., in units of carat) to data processor 30 by means of communication system 28. The operation of gemstone scale 74 is optionally and preferably controlled by controller 80. Gemstone scale 74 can be positioned within cavity 46, for example, below cavity 46, in which case gemstone scale 74 is calibrated to subtract the weight of cavity 46 to provide the net mass of gemstone 14.

Once processor 30 obtains the gemstone characteristics (color grade and/or clarity grade), processor 30 can accesses an online gemstone market value database, search the database for gemstone characteristics that match the obtained gemstone characteristics and pull a market value or a range of market values that corresponds to the matched gemstone characteristics. Processor 30 can then generate an output pertaining to the pulled market value or range of market values, for example, on display 40. When processor 30 receives input pertaining also to the cut, mass, fluorescence strength, and/or other properties of gemstone 14, the output can include the absolute market value or range of market values. When cut input is not available, the output can include a set of market values or a set of ranges of market values, one market value or range of market values for each of a plurality of cuts.

Library 44 can be prepared by operating a system such as system 10 to sequentially determine the transmittance spectra of a plurality of gemstones for which the gemstone characteristics (color grades and/or clarity grades and/or fluorescence), and optionally also other gemstone properties (e.g., cut, mass) are known, for example, as an input from a human gemologist, and recording in library 44 the determined transmittance spectra and the known gemstone characteristics and properties. The use of such library is particularly useful since it allows determining the gemstone characteristics (color and/or clarity grades) even when some deviations from ideality are present. This is because the same system or the same type of system is used both for generating the library, and for determining the gemstone characteristics of a test gemstone. In particular, this allows system 10 to grade also cut gemstones since it is expected that the transmittance spectrum that is provided by data processor using the technique of the present embodiments is repeatable if executed for the same or similar cut, mass, color grade and/or clarity grade.

The imaging data provided by system 72 and/or the signals provided by gemstone scale 74 (in embodiments in which one or both these system components are employed) can alternatively or additionally be used by controller 80 to determine whether or not a gemstone is present in cavity 46. Also contemplated are embodiments in which system 10 comprises a presence sensor 78 configured to transmit to controller 80 signals pertaining to the presence or absence of the gemstone in cavity 46. In response to an indication that a gemstone is present in cavity 46, controller 80 can automatically activate various components of system 10 (e.g., light sources 12, modulator 16). Conversely, in response to an indication that a gemstone is not present in cavity 46, controller 80 can deactivate light sources 12 and/or modulator 16. When it is desired to determine the presence or absence of a gemstone in cavity 46 based on image data, controller 80 is preferably provided with an image processing circuit configured to process and analyze the image data and to determine the presence or absence of the gemstone. Controller 80 can also be configured to change the power consumption level of various components of system 10 in response to a determination that no gemstone is present in cavity 46 and/or in response to a determination that the system is not in use for a period of time which is above a predetermined threshold.

In embodiments in which detection system 18, and optionally also detection system 26, comprises a pixilated light sensor (e.g., pixilated light sensor 20, FIGS. 2A and 2B) the spectral decomposition provided by detection system 18 can improve the spectral sensitivity and accuracy of system 10, for example, when a particular illumination light source has a spectral width that is wider than the spectral width of the filters mounted on the pixilated light sensor. Further, the number of different filters on the pixilated light sensor can be larger than the number of distinguishable wavelengths provided by the light sources. For example, when the spectral width of a particular light source spans over a wavelength range encompassing two spectral widths of the pixilated light sensor, the pixilated light sensor can improve (e.g., double) the spectral resolution provided by the particular light source. The use of the pixilated light sensor can therefore provide more detailed information regarding the transmittance spectrum of the gemstone, because it allows determining the transmission in more and narrower wavelength bands. In various exemplary embodiments of the invention for each of at least one of light sources 12, two or more of the pixels of the pixilated light sensor spectrally decompose the illumination wavelength band provided by the respective light source into respective two or more wavelength sub-bands.

The present inventor also contemplates embodiments in which some or all of the decomposition is done solely by the pixilated light sensor. In these embodiments, system 10 comprises a plurality of monochromatic light sources, such as light sources 12 arranged to simultaneously illuminate gemstone 14 by light, a light detection system, such as light detection system 18 for collecting light following interaction of the light with gemstone 14, where light detection system 18 comprises a pixilated light sensor, such as sensor 20 configured to sense different wavelengths by different pixels of sensor, and a communication system 28 configured to communicate signals from light detection system 18 to a data processor, such as data processor 30 for extracting from the signals a transmittance spectrum 38, and for generating an output indicative of the transmittance spectrum. In these embodiments, it is not necessary for system to include a modulator that provides spectral-specific modulation, since the decomposition into the spectral component is provided by the pixilated light sensor. Thus, the modulator in these embodiments can provide the same modulation to all the spectral bands. Also contemplated, are embodiments in which there is no modulation, in which case the light sources are operated in DC mode. It is noted that the modulation of the illumination source may also discriminate between the ambient light and the system's illumination and improve the measurement accuracy as further detailed hereinbelow.

In the embodiments in which there is no spectral-specific modulation, signals pertaining to spectral components as decomposed by the pixilated light sensor are transmitted by the communication system to the data processor. The data processor receives the signals and optionally and preferably performs calibration as further detailed hereinabove to provide a transmittance spectrum as a function of the wavelength or optical frequency. The library is searched for a matching library-stored transmittance spectrum, and gemstone characteristics (color grade and/or clarity grade etc.) is pulled as further detailed hereinabove.

The inventor discovered that operating the light sources simultaneously is advantageous over a process in which the light sources are operated sequentially, for the reasons that will now be explained.

Figure 5:
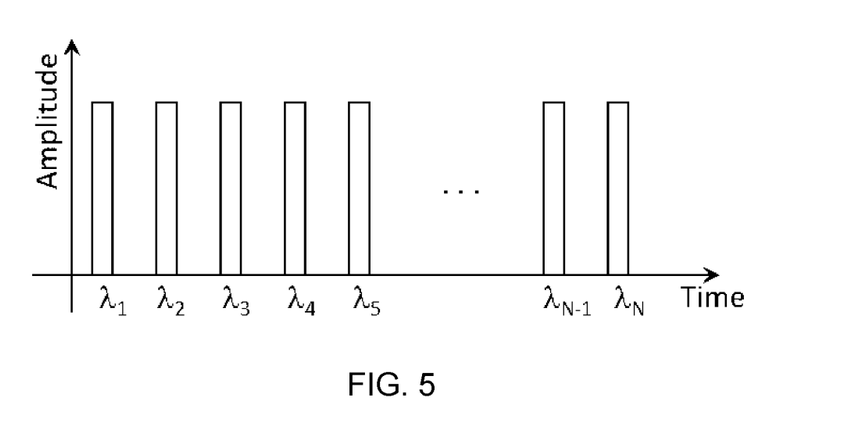
FIG. 5 schematic temporal diagram illustrating a sequential schedule for activating N LEDs.

Suppose, for example, that there are N different light sources. Conventional sensing systems, such as the systems described in Hardie et al., and O'Toole et al., supra, turn on N LEDs sequentially in accordance with the temporal diagram shown in FIG. 5. Suppose further that the digitization of the sensor is characterized by M levels and its total operation range is U, so that the error of single amplitude measurement is U/2 M.

When all light sources are operated simultaneously and modulated non-synchronously, in accordance with some embodiments of the present invention, their mean total amplitude is expected to be about U√N. The error of the amplitude reconstruction of a particular signal oscillating at any frequency is given by:

$$S = \frac{U\sqrt{N}}{2M \cdot \sqrt{N_s}}$$

where, $N_s$ is the number of samples provided by the digitization (e.g., by means of A2D circuit 24). $N_s$ relates to the sampling rate $f_s$, and the duration T within which the sources operate, through the relation $N_s = T \cdot f_s$. As a representative example that is not to be considered as limiting, consider the case in which N=10, T=1 sec, and $f_s$=4096 Hz. Substituting these values in the above expression for S, one gets S=0.05 (U/2 M), namely accuracy that is about 20 times better than the accuracy that is obtainable when the light sources are activated sequentially (with error U/2 M). As an additional example, consider the case in which T=0.1 sec. In this case the measurement error is S=0.16 (U/2 M), which is about 6 times smaller than the error achieved in the sequential case. A similar result can be obtained for the case all the light sources modulated at the same frequency. Therefore, the simultaneous operation of the light sources according to some embodiments of the present invention is advantageous because it improves the accuracy of the results with respect to the sequential light source operation.

Another drawback of the application of the sequential operation of the light sources is that such operation cannot allow measuring with an open cavity under ambient light blinking due to the electric power grid frequency (e.g., 50 Hz, 60 Hz and their harmonics). The modulation at frequencies that differ from the electric power grid frequency and its harmonics, in accordance with some embodiments of the present invention, obviates this drawback since the ambient light blinking does not affect the set of modulation intensities that relate to the values of the modulation parameter that characterize the modulation applied by modulator 16.

A further advantage of operating the light sources simultaneously in accordance with some embodiments of the present invention is that the light conditions are stabilized quicker compared to systems in which sequential activation of light sources is employed. The reason is that the light source temperature changes with the turning on of the light sources. Simultaneous turning on of all the light sources causes simultaneous thermal effect on light intensity of the light sources. On the other hand, the sequential turning on of the light sources cause that the 1st light source (LED, lasers etc) begins its operation at the room temperature, while the last light source operates later as heated by the previous. The illumination characteristics of the light sources is thus not uniform and equilibrium is not achieved until certain amount of time has passed. The simultaneous operation of the light sources according to the present embodiments ensures that all the light sources undergo the same heating.

Figure 6A:
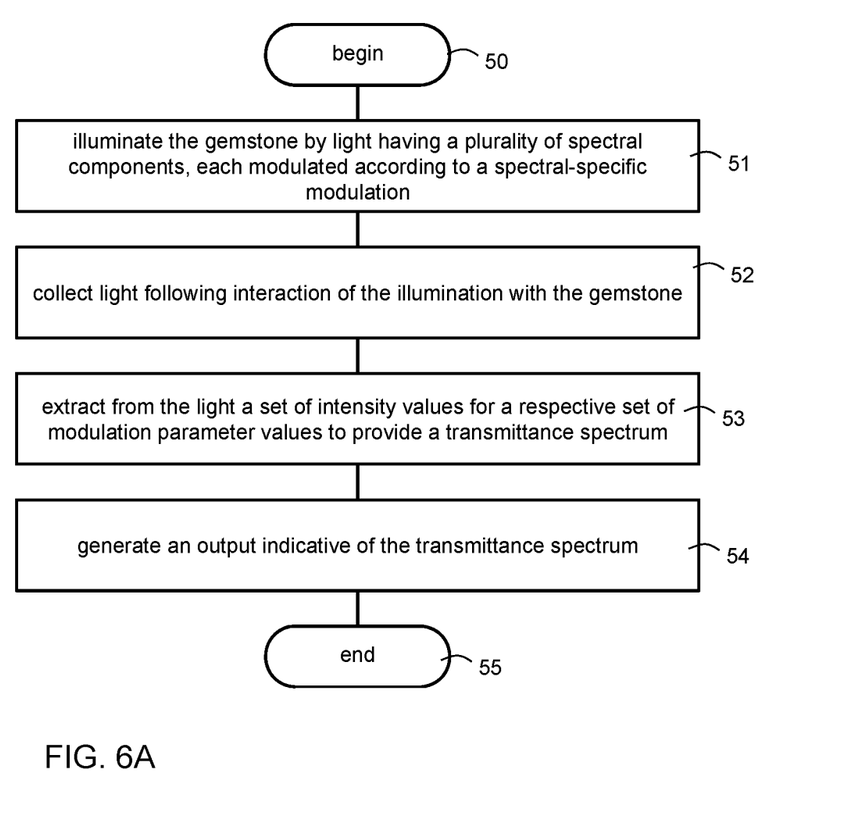
FIGS. 6A and 6B are flowchart diagrams of a method suitable for grading a gemstone according to various exemplary embodiments of the present invention.
Figure 6B:
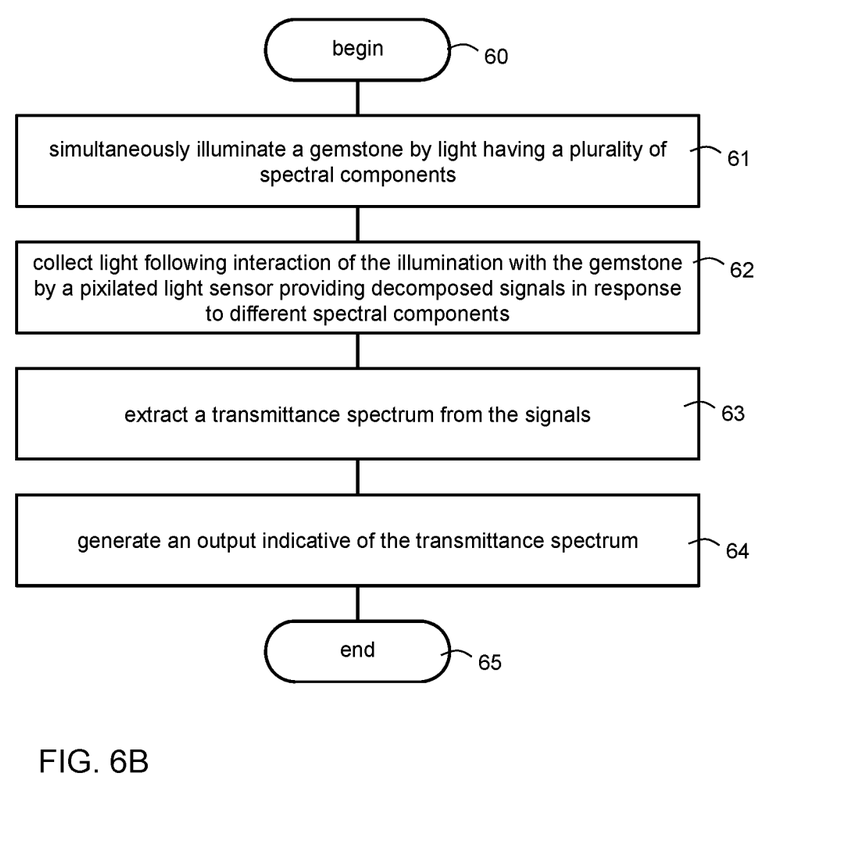

FIGS. 6A and 6B are flowchart diagrams of a method suitable for grading a gemstone according to various exemplary embodiments of the present invention. The method can be executed using a system such as, but not limited to, system 10. Preferably, once the gemstone is placed in the system, and the system is activated the gemstone's grade or grades is provided automatically without further user intervention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Referring to FIG. 6A, the method begins at 50 and continues to 51 at which the gemstone is illuminated by light having a plurality of spectral components, each modulated according to a spectral-specific modulation, as further detailed hereinabove. The method proceeds to 52 at which the light is collected following its interaction with the gemstone, as further detailed hereinabove. At 53 a set of intensity values for a respective set of modulation parameter values is extracted from the collected light, to provide a transmittance spectrum, as further detailed hereinabove, and at 54 an output indicative of the transmittance spectrum is generated as further detailed hereinabove.

The method ends at 55.

Referring to FIG. 6B, the method begins at 60 and continues to 61 at which the gemstone is simultaneously illuminated by light having a plurality of spectral components. The method continues to 62 at which the light is collected, following its interaction with the gemstone, by a pixilated light sensor configured to sense different spectral components by different pixels of the sensor and to responsively provide separate signals, as further detailed hereinabove. At 63, a transmittance spectrum is extracting from the signals as further detailed hereinabove, and at 64 an output indicative of the transmittance spectrum is generated as further detailed hereinabove.

The gemstone color optionally and preferably be further evaluated to any acceptable charts or decompositions describing the color, such as the CIE color space or other.

The method ends at 65.

In some embodiments of the present invention the execution time of the method, from the time at which the gemstone is positioned in cavity 46 to the time at which the output is generated, is less than 1 second, or less than 0.8 seconds, or less than 0.6 seconds, or less than 0.4 seconds, or less than 0.2 seconds, e.g., about 0.1 seconds or less.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

An experimental system included LEDs of different wavelength characteristics including central wavelength and wavelength bandwidth. A set of LEDs with similar characteristics may be operated together at the similar electrical conditions and similar electrical signals may be applied to all the LEDs in the set. The set were interlaced with each other to form groups of LEDs.

In some experiments each set of LEDs was operated at amplitude modulation with frequencies different for each set but the same for all LEDs in the set. The modulation frequencies were not harmonics of one another or harmonics of the electric power grid to avoid mutual disturbances.

Figure 7A:
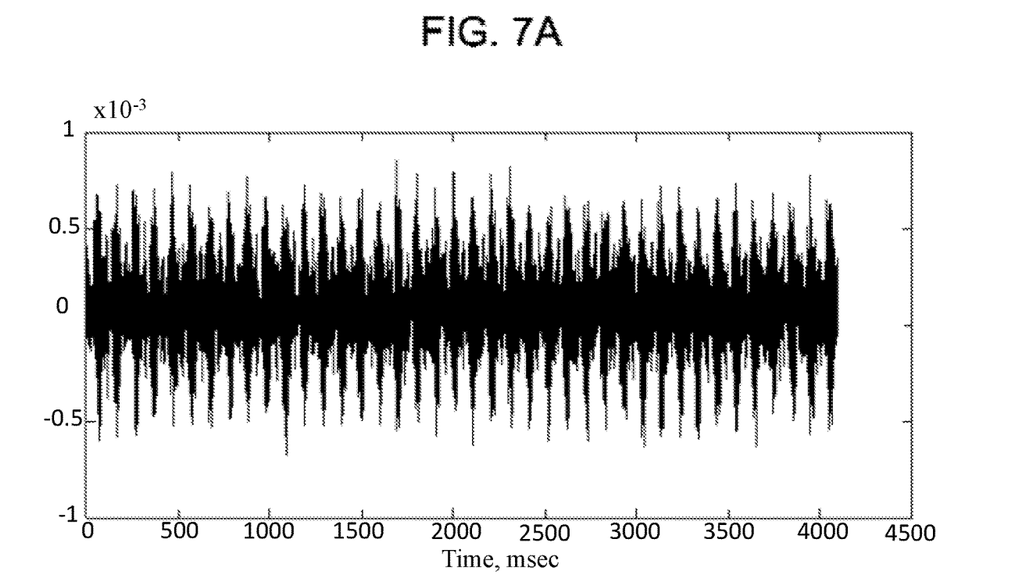
FIG. 7A shows an experimental record of signals recorded in an experiment performed according to some embodiments of the present invention.

FIG. 7A shows an experimental record of the signals. The illumination was carried out by means of three sets of LEDs, arranged in an interlaced manner. The First set included LEDs that have central wavelength 470 nm, FWHM=30 nm. This set was modulated sinusoidally at frequency f1=370 Hz. The second set included LEDs that have central wavelength 550 nm, FWHM=30 nm. This set was modulated sinusoidally at frequency f1=390 Hz. The third set included LEDs that have central wavelength 630 nm, FWHM=30 nm. This set was modulated sinusoidally at frequency f1=410 Hz. In the interlaced arrangement, each group of LEDs was a triplet of LEDs, one LED from the first set, one LED from the second set, and one LED from the third set, as illustrated in FIG. 1B.

The employed frequencies are not harmonics of one another and do not have harmonic relation to the electric power grid frequency of 50 Hz.

The detector collected the light emitted by all the LEDs and, following an A2D, transmitted to a computer or smartphone for further signal processing.

Figure 7B:
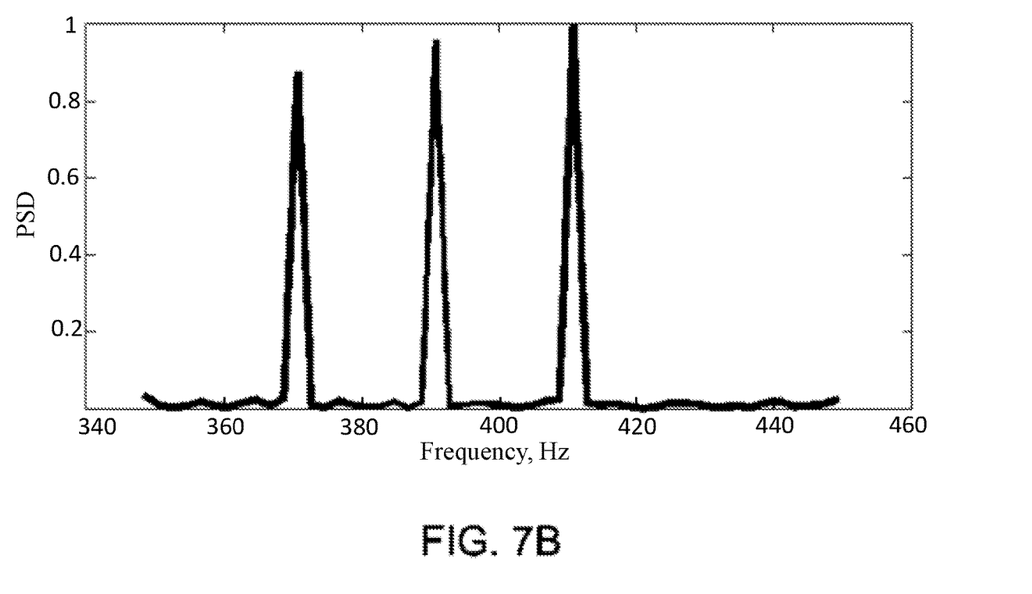
FIG. 7B shows a Fourier transform of the signal of FIG. 7A, as obtained in an experiment performed according to some embodiments of the present invention.

The recorded signal was analyzed by Fourier technique. FIG. 7B shows a Fourier transform of the signal of FIG. 7A. Each peak in the graph corresponds to different modulation frequency of the set of LEDs and is therefore associated with a specific wavelength characteristics of the LEDs in the set. The comparison of the peak intensity at the specific frequency before the stone introduction and after its introduction may provide the transmittance of the stone at the wavelength characterizing the specific LED group. Otherwise, the comparison may be evaluated between transmission characteristics of the ideal transparent gemstone of diamond and another tested gemstone. The gemstone's spectral characteristics and its color grading may be referred to this master stone.

This Example demonstrates the ability of the present embodiments to determine the spectral components of modulated light emitted from a plurality of light sources.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A system for grading gemstones, comprising:
a plurality of monochromatic light sources arranged to simultaneously illuminate a gemstone;
a light modulator for modulating light emitted by each light source on said gemstone to provide illumination that is modulated according to a spectral-specific modulation;
a light detection system for collecting light following interaction of said simultaneous modulated illumination with said gemstone; and
a communication system configured to communicate signals from said light detection system to a data processor for extracting from said signals a set of intensity values for a respective set of modulation parameter values to provide a transmittance spectrum, and for generating an output indicative of said transmittance spectrum.

2. The system according to claim 1, wherein said spectral-specific modulation is selected from the group consisting of intensity modulation, frequency modulation, and phase modulation.

3. The system according to claim 1, wherein said light modulator comprises at least one of:
a light modulator configured to provide modulation according to the same modulation scheme, but using different values of said modulation parameter for different spectral components of said light;
a light modulator configured to modulate said light such that modulations of different spectral components are characterized by a different modulation frequency; and
a light modulator configured to modulate said light with a modulation frequency other than a frequency of an electric power grid operating in a vicinity of said system, and other than each harmonic of said electric power grid.

4. The system according to claim 1, wherein said light detection system comprises a pixilated light sensor configured to sense different spectral components by different pixels of said sensor.

5. The system according to claim 1, wherein said output comprises at least one of: a color grade of said gemstone; and a graphical representation of said transmittance spectrum.

6. The system according to claim 1, further comprising a reference light detection system for collecting light that does not interact with said gemstone, wherein said data processor is configured for receiving reference signals from said reference light detection system and calibrating said transmittance spectrum or said output based on said reference signals.

7. The system according to claim 1, wherein said data processor comprises at least one of:
a data processor is comprised as a component of said system;
a data processor comprising a central processing unit of a mobile device;
a data processor configured for calibrating said transmittance spectrum or said output based on pre-recorded calibration data;
a data processor configured to calculate a clarity grade of said gemstone based on reference signals, and wherein said output is also indicative of said clarity, wherein said system further comprises a reference light detection system for collecting light that does not interact with said gemstone, wherein said data processor is configured for receiving said reference signals from said reference light detection system and calibrating said transmittance spectrum or said output based on said reference signals; and
said data processor is configured to calculate a clarity grade of said gemstone based on said pre-recorded calibration data, and wherein said output is also indicative of said clarity.

8. The system according to claim 1, further comprising a cavity for holding said gemstone, wherein said cavity comprises a closed cavity or an open cavity.

9. The system according to claim 1, wherein said light sources are selected from the list including:
- light sources comprising at least one ultraviolet light source, wherein said output comprises a fluorescence strength of said gemstone;
- light sources arranged peripherally with respect to said gemstone; and
- light sources arranged in an interlaced manner to define a plurality of light source groups, each comprising a plurality of light sources, wherein for each group of said plurality of light source groups at least two light sources of said group provide different spectral components.

10. The system according to claim 1, further comprising a light manipulating element positioned at a light path of light to be detected by the detection system, wherein said light manipulating element comprises at least one selected from the list of: a non-optical light manipulating element; an optical element selected from the group consisting of a polarizer, a diffuser, a lens, a filter, and a refractor.

11. A method of grading a gemstone, comprising:
- illuminating the gemstone by light, said light simultaneously having a plurality of spectral components, each modulated according to a spectral-specific modulation;
- collecting light following interaction of said plurality of spectral components with the gemstone;
- extracting from said collected light a set of intensity values for a respective set of modulation parameter values to provide a transmittance spectrum; and
- generating an output indicative of said transmittance spectrum.

12. The method of claim 11, wherein said spectral-specific modulation is selected from the group consisting of intensity modulation, frequency modulation, and phase modulation.

13. The method of claim 11, wherein said spectral-specific modulation comprises at least one selected from the list of:
- a spectral-specific modulation wherein each spectral component is modulated according to the same modulation scheme, but using different values of said modulation parameter for different spectral components;
- a spectral-specific modulation wherein different spectral components are modulated using different modulation frequencies; and
- a spectral-specific modulation wherein each modulation frequency is other than a frequency of an electric power grid operating in a vicinity of said system, and other than each harmonic of said electric power grid.

14. The method according to claim 11, wherein said collecting is operated by a pixilated light sensor configured to sense different spectral components by different pixels of said sensor.

15. The method according to claim 11, wherein said output comprises at least one of: a color grade of said gemstone; and a graphical representation of said transmittance spectrum.

16. The method according to claim 11, further comprising at least one procedure selected from the list of:
- collecting reference light that does not interact with said gemstone, and calibrating said transmittance spectrum or said output based on said reference light;
- calculating a clarity grade of said gemstone based on said reference light, wherein said output is also indicative of said clarity;
- calibrating said transmittance spectrum or said output based on pre-recorded calibration data; and
- calculating a clarity grade of said gemstone based on said pre-recorded calibration data, wherein said output is also indicative of said clarity.

17. The method according to claim 11, further comprising placing the gemstone in an open cavity prior to said interaction with said light, wherein said illumination is executed while said cavity is open.

18. The method according to claim 11, wherein said illumination is operated by a plurality of light sources arranged in an interlaced manner to define a plurality of light source groups, each comprising a plurality of light sources, wherein for each group of said plurality of light source groups at least two light sources of said group provide different spectral components.

19. The method according to claim 11, further comprising a manipulating said light following said interaction and prior to said collecting, wherein said manipulating comprises at least one of: non-optical manipulating, polarizing, diffusing, focusing, collimating, filtering, and refracting.

20. The method according to claim 11, wherein said extracting and said generating said output is operated by a central processing unit of a mobile device.

* * * * *